United States Patent
Sudo

[11] Patent Number: 5,951,527
[45] Date of Patent: Sep. 14, 1999

[54] SLIDING PISTON FOR SYRINGE

[75] Inventor: Morihiro Sudo, Tokyo, Japan

[73] Assignee: Daikyo Seiko, Ltd, Tokyo, Japan

[21] Appl. No.: 09/073,374

[22] Filed: May 5, 1998

[51] Int. Cl.$^6$ .................................................. A61M 5/315
[52] U.S. Cl. .......................... 604/218; 604/228; 604/230
[58] Field of Search .............................. 604/89–91, 218, 604/219, 224, 228, 187, 230

[56] References Cited

U.S. PATENT DOCUMENTS

| | | | |
|---|---|---|---|
| 4,747,838 | 5/1988 | Wolff et al. | 604/218 |
| 4,986,820 | 1/1991 | Fischer | 604/218 |
| 5,743,890 | 4/1998 | Hjertman et al. | 604/218 |
| 5,782,815 | 7/1998 | Yanai et al. | 604/218 |

Primary Examiner—Ronald Stright, Jr.
Assistant Examiner—Michael J. Hayes
Attorney, Agent, or Firm—McCormick, Paulding & Huber LLP

[57] ABSTRACT

A sliding piston for a syringe, which is inserted in a hollow barrel of a syringe is made of a substantially cylindrical body having a shape symmetrically rotatable with respect to the axis of the hollow barrel. The cylindrical body has its largest diameter at the front end thereof. The peripheral edge of the front end of the cylindrical body is rounded at a radius of curvature of $5/100$ mm to $10/100$ mm. The diameter of the rear end of the cylindrical body is smaller than the inner diameter of the hollow barrel so as not to contact with the inner surface of the hollow barrel when the piston is inserted in the hollow barrel.

12 Claims, 2 Drawing Sheets

SLIDING PISTON FOR SYRINGE

BACKGROUND OF THE INVENTION

1. Field of the Invention

The present invention relates to a sliding piston for a syringe, which is slidably inserted in a hollow barrel to inject a liquid medicament contained in the hollow barrel into a human or animal body.

2. Description of the Related Art

A syringe is essentially composed of a hollow barrel (tubular body), a sliding piston and a plunger. Upon injection of a liquid medicament, the sliding piston is moved by the plunger to inject the liquid medicament contained in the hollow barrel. The sliding piston must be tightly fitted in the hollow barrel to be liquid-tight and air-tight fashion so as to smoothly slide therein even when the sliding piston is moved forward or rearward in the hollow barrel held in an inclined angle. The hollow barrel is usually made of glass or plastic. In general, the glass barrel is used also as a container for a liquid medicament, and the plastic barrel is used for a single-use type or disposable type syringe. In either barrel, the inner diameter, linearity, surface smoothness, and the roundness, of the hollow barrels are inevitably irregular to some extent due to manufacturing error.

The sliding piston is usually made of a resilient material, such as rubber or thermoplastic elastomer, to absorb the irregularity in the shape of the hollow barrel. The conventional resilient piston (rubber bulb) is in the form of a simple cylinder, a truncated cone whose diameter is gradually decreased toward the rear end, or a cylinder or truncated cone with annular projections at the front and rear ends thereof. However, according to the inventor's analysis, the conventional resilient piston can be still improve its physical properties, and in particular, slidability and air-tightness.

In particular, in a laminated piston proposed by the assignee of the present application, in which the surface of the resilient piston is coated with a laminated layer selected from a group of tetrafluoroethylene, ethylene-tetrafluoroethylene and supermacromolecular polyethylene resin films, the elastic compliance of the resilient piston tends to be reduced due to the laminated layer. To solve this problem, the physical properties of the sliding piston must be improved. The proposed laminated piston is of a silicone-free type in which it is not necessary to coat the sliding portion with a silicone oil layer as a lubricant. In the conventional sliding piston which is coated with the silicone lubricant, there is a possibility that the silicone oils mix with the liquid medicament and contaminate the liquid medicament with the particulate.

SUMMARY OF THE INVENTION

It is an object of the present invention to provide a sliding piston for a syringe, which exhibits good physical properties, and particularly improved air-tightness and enhanced slidability.

To achieve the object mentioned above, according to the present invention, a sliding piston is provided which is inserted in a hollow barrel of a syringe. The piston is a substantially cylindrical body having a shape which is rotatably symmetrical with respect to the axis of the hollow barrel. The cylindrical body has its largest diameter at the front end thereof, the peripheral edge of the front end of the cylindrical body is rounded at a radius of $5/100$ mm to $10/100$ mm in cross section, and the diameter of the rear end of the cylindrical body is smaller than the inner diameter of the hollow barrel so as not to contact with the inner surface of the hollow barrel when the piston is inserted in the hollow barrel.

Preferably, the substantially cylindrical body is provided with a first reduced portion whose diameter is reduced from the front end to an intermediate portion and a second reduced portion whose diameter is reduced from the intermediate portion to the rear end, the degree of reduction in diameter of the second reduced portion being greater than that of the first reduced portion.

Preferably, the contours of the first and second reduced portions in a longitudinal section taken along a plane including the longitudinal axis of the cylindrical body are defined by a straight line and an arc, respectively.

Preferably, the front end of the substantially cylindrical body is provided with a flat conical surface.

According to an embodiment the sliding piston constitutes an elastic body and a laminated layer thereon. The laminated layer is made of a film selected from a group of tetrafluoroethylene, ethylene-tetrafluoroethylene and supermacromolecular polyethylene resin films.

The amount of allowable deformation is preferably in the range of $3/100$ to $15/100$ mm, if the inner diameter of the hollow barrel is in the range of 7.0 to 32.0 mm. The taper angle of the first reduced portion which represents the degree of reduction is preferably in the range of 0.5° to 3.0°.

Preferably, the ratio in the axial length between the first and second reduced portions is in the range of 0.6–0.9:1, so that the first reduced portion is in contact with the hollow barrel and the second reduced portion is not in contact with the hollow barrel when the piston is inserted in the hollow barrel. Consequently, the slidability and the air-tightness can be enhanced in a well-balanced state.

The front end of the substantially cylindrical body can be provided with a surrounding annular flat surface portion substantially perpendicular to the axis of the cylindrical body and a center truncated conical surface portion. With this arrangement, in particular, a smooth drawing motion of the piston can be obtained.

The cylindrical body can be provided on the rear end thereof with a threaded hole in which a plunger can be screwed. The minimum thickness defined by the distance of the outer peripheral surface from the peripheral surface of the threaded hole is preferably in the range of 1.0 mm to 4.0 mm.

According to another aspect of the present invention there is provided a syringe including a hollow barrel, a sliding piston which is inserted in said hollow barrel and a plunger which is screwed in said sliding piston. The piston constitutes a cylindrical body, having the largest diameter at the front end thereof and a threaded hole at the rear end thereof in which the plunger is screwed. The peripheral edge of the front end of the cylindrical body is rounded at a radius of curvature of $5/100$ to $10/100$ mm in cross section. The diameter of the rear end of the cylindrical body is smaller than the inner diameter of the hollow barrel so as not to contact with the inner surface of the hollow barrel when the cylindrical body is inserted in the hollow barrel.

Preferably, the cylindrical body is provided with a first reduced portion whose diameter is reduced from the front end to an intermediate portion and a second reduced portion whose diameter is reduced from the intermediate portion to the rear end, so that the first reduced portion is in contact with the hollow barrel and the second reduced portion is not in contact with the hollow barrel when the piston is inserted in the hollow barrel.

In an embodiment applied to a silicone-free piston, i.e., a laminated sliding piston, it is preferably composed of an elastic body and a laminated layer thereon, made of a film selected from the group of a tetrafluoroethylene resin film, an ethylene-tetrafluoroethylene resin film and a supermacromolecular polyethylene resin film.

The present disclosure relates to subject matter contained in Japanese Patent Application No. 08-156535 (filed on Jun. 18, 1996) which is expressly incorporated herein by reference in its entirety.

BRIEF DESCRIPTION OF THE DRAWINGS

The invention will be discussed below in detail with reference to the accompanying drawings, in which.

DESCRIPTION OF THE PREFERRED EMBODIMENT

Figure 1:
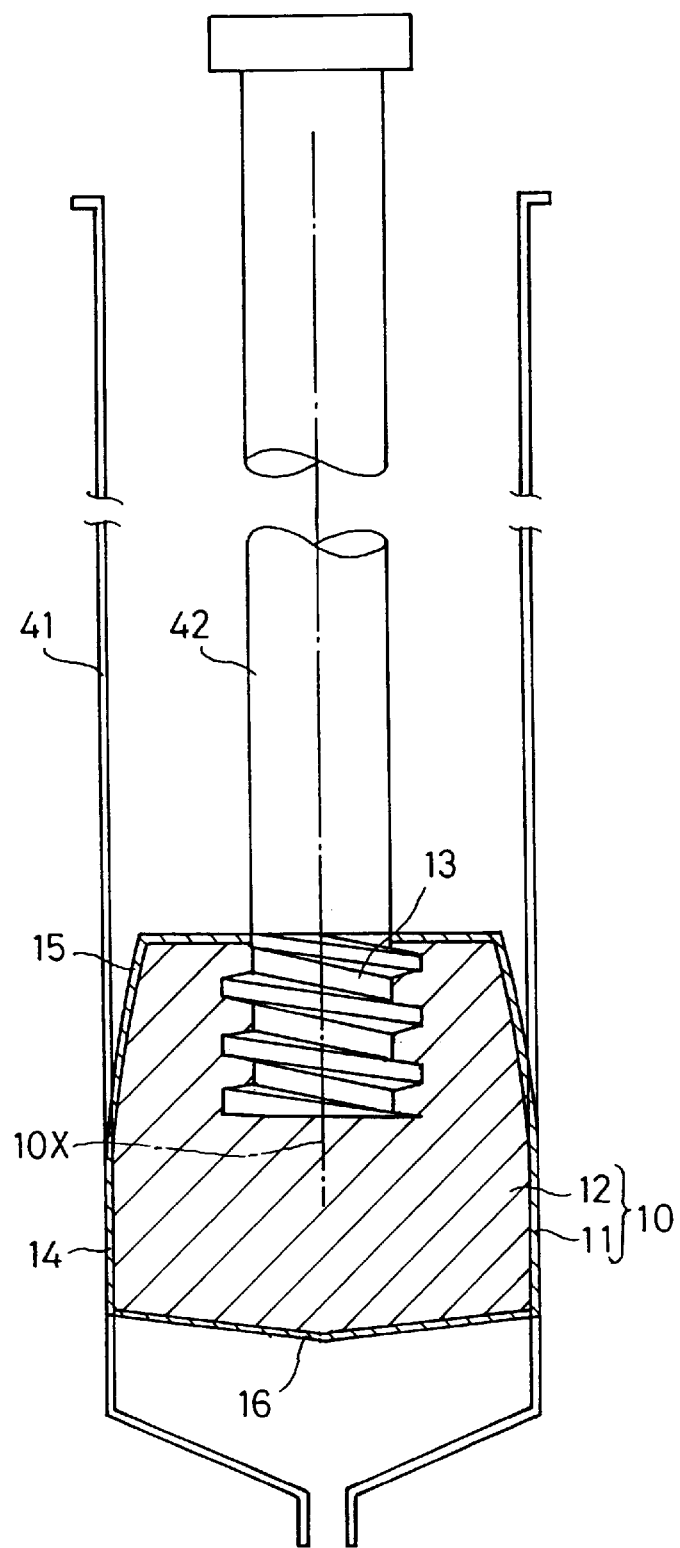
FIG. 1 is a longitudinal sectional view of a sliding piston for a syringe, which exhibits good physical properties and in particular, an enhanced air-tightness and a good slidability, according to an embodiment of the present invention.
Figure 2:
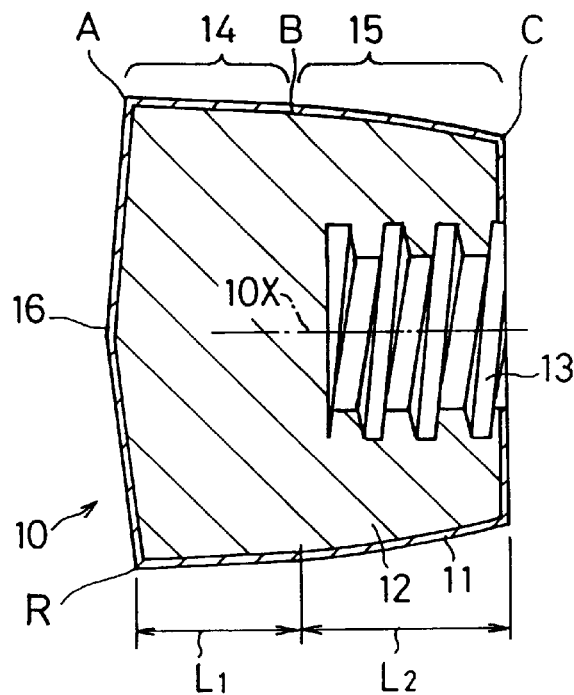
FIG. 2 is an enlarged sectional view of a sliding piston for a syringe shown in FIG. 1; and, FIG. 3 is an enlarged sectional view of a sliding piston for a syringe, according to another embodiment of the present invention.

FIGS. 1 and 2 shows a first embodiment of the present invention, applied to a laminated piston. The laminated piston 10 is composed of an elastic body 12 made of rubber or thermoplastic elastomer and a laminated layer 11 which is coated on the surface of the elastic body 12 including at least the outer peripheral surface and the front end surface thereof. The laminated layer 11 is made of a film selected from the group of tetrafluoroethylene, ethylene-tetrafluoroethylene and supermacromolecular polyethylene resin films. The thickness of the laminated layer 11 is preferably in the range of 0.001 mm to 0.2 mm. The elastic body 12 of the laminated piston 10 is provided with a threaded hole 13 in which a plunger 42 is screwed, so that the elastic body 12 can be slidably inserted in a hollow barrel 41 of a syringe.

The laminated piston 10 is made of a substantially cylindrical body having a shape which is rotatably symmetrical with respect to the axis 10X thereof and is provided with a first reduced portion 14 and a second reduced portion 15. The diameter of the first reduced portion 14 is gradually decreased from the tip end "A" to the intermediate portion "B". The diameter of the second reduced portion 15 is gradually decreased from the intermediate portion "B" to the rear end "C". The diameter of the first reduced portion 14 in a free state is larger than the inner diameter of the hollow barrel 41, so that when the piston 10 is inserted in the hollow barrel 41, the first reduced portion 14 is elastically deformed. The difference in the diameter between the first reduced portion and the hollow barrel is preferably in the range of 3/100 mm to 15/100 mm.

The contours of the first and second reduced portions 14 and 15 in a longitudinal section taken along a plane including the axis 10X consist of a straight line and a curved line (arc), respectively. The inclination angle (taper) of the straight line with respect to the axis 10X defining the first reduced portion 14 is in the range of 0.5° to 3.0° taking into account the diameter and length of the sliding piston 10. The radius of curvature of the arc defining the second reduced portion 15 is determined so that the degree of reduction of the second reduced portion 15 is greater than that of the first reduced portion 14 so as to prevent the rear end of the second reduced portion 15 from interfering with the hollow barrel 41. If the taper of the first reduced portion 14 is smaller than 0.5°, it is difficult to obtain a sufficient contact pressure (sliding pressure) at the front end. If the taper is larger than 3.0°, no uniform deformation of the first reduced portion 14 with respect to the hollow barrel 41 takes place in the axial direction thereof, thus not resulting in a smooth sliding movement of the sliding piston. If the degree of reduction of the second reduced portion 15 is less than that of the first reduced portion 14, it is difficult to keep the entire second reduced portion 15 in non-contact with the hollow barrel 41, and consequently, a smooth sliding movement of the piston cannot be achieved. Moreover, a burr tends to be produced at the rear end of the second reduced portion 15 upon manufacturing of the piston. To prevent the rear end of the second reduced portion 15 (laminated piston 10) from coming into contact with the hollow tube 41 of the syringe even if the burr is produced at the rear end, the degree of reduction of the second reduced portion 15 is greater than that of the first reduced portion 14, as mentioned above. Namely, the diameter of the rear end "C" of the second reduced portion 15 is small enough to prevent the rear end from coming into contact with the hollow barrel 41 of the syringe when the piston 10 is inserted in the hollow barrel 41.

The corner edge R of the front end "A" of the first reduced portion 14 is slightly rounded at a radius of curvature of 5/100 mm to 10/100 mm. The front end of the piston 10 is defined by a substantially flattened cone 16 whose apex is located on the axis 10X of the piston 10 and which projects forward.

As can be seen from the foregoing, since the largest diameter portion of the piston 10 is provided on the front end thereof and the front end edge R (of the first reduced portion 14) is slightly rounded, a smooth sliding movement of the piston can be ensured. The reason why the piston can smoothly move in the hollow barrel can be assumed as follows. Namely, the diameter of the first reduced portion 14 at its free state is larger than the inner diameter of the hollow barrel 41 (plus-fit). If the radius of curvature of the rounded corner is large as in the conventional piston, the contact surface area of the rounded corner with the inner surface of the hollow barrel 41 is increased. However, if the radius of curvature of the rounded corner is small as in the present embodiment and as mentioned above, the contact surface area of the rounded corner with the inner surface of the hollow barrel 41 is decreased, so that a smooth movement can be obtained. Moreover, if the rounded corner R is small as mentioned above, no or a negligible amount of liquid medicament can enter the surrounding portion of the front end of the laminated piston 10, and hence no build-up of liquid medicament is produced in the surrounding portion of the front end of the laminated piston 10, thus leading to a reliable and safe operation of the syringe.

Moreover, since the rear end of the piston is smaller than the inner diameter of the hollow barrel 41, no 'knocking' occurs, in particular upon drawing the piston. This is because the rear end of the second reduced portion 15 which tends to have a burr produced thereon upon manufacturing, as mentioned above, does not contact with the inner surface of the hollow barrel 41. The absence of knocking also contributes to a smooth sliding motion of the piston.

It is possible to define the size of the rear end of the laminated piston 10 by the minimum thickness of the rear end defined by the distance between the peripheral wall surface of the threaded hole 13 and the outer peripheral surface of the laminated piston 10. The minimum thickness is preferably in the range of 1.0 mm to 4.0 mm.

The ratio between the axial lengths L1 and L2 of the first and second reduced portions 14 and 15 is preferably in the range of 0.6:1 to 0.9:1. If the length L2 is shorter than the length L1, there is a possibility that the burr comes into contact with the inner surface of the hollow barrel 41, so that a smooth sliding motion of the piston cannot be ensured. If the length L1 is too long, the sliding resistance is increased, thus resulting in a reduced operability and in a difficulty in inserting the piston into the hollow barrel 41 by machine.

Figure 3:
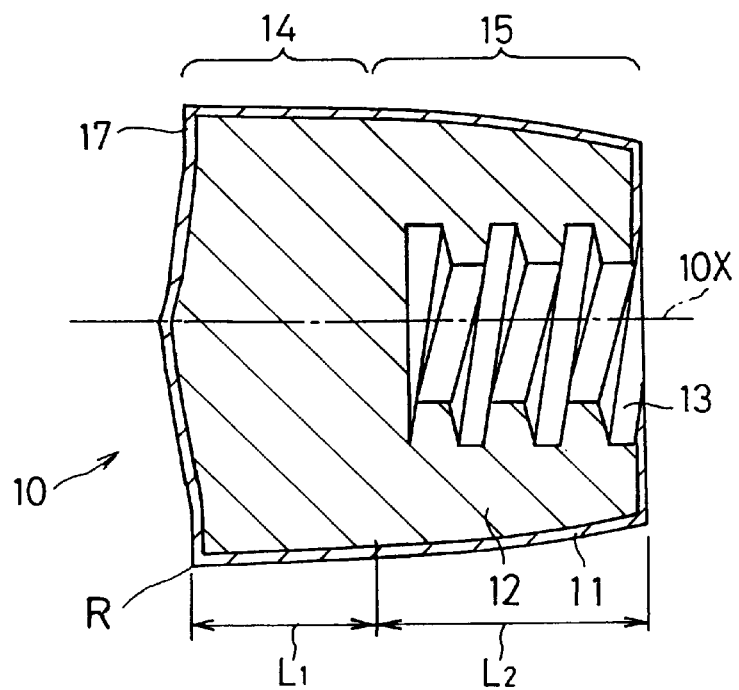

FIG. 3 shows another embodiment of a sliding piston according to the present invention. In this embodiment, the shape of the front end of the laminated piston 10 is different from that shown in FIG. 2. The front end surface of the laminated piston 10 consists of a surrounding annular flat surface portion 17 substantially perpendicular to the axis 10X and a central substantially flattened cone surface portion 16 whose axis is identical to the axis 10X and which projects forward. The second embodiment shown in FIG. 3 ensures a smooth sliding motion of the piston particularly when the piston is drawn.

As can be understood from the above discussion, according to the present invention, a sliding piston for a syringe which exhibits good physical properties and particularly improved air-tightness and high slidability can be provided.

Although the invention has been described with reference to particular means, materials and embodiments, it is to be understood that the invention is not limited to the particulars disclosed and extends to all equivalents within the scope of the claims.

What is claimed is:

1. A sliding piston which is inserted in a hollow barrel of a syringe, said piston being in the form of a substantially cylindrical body having a symmetrically rotatable shape with respect to the axis of the hollow barrel;

said cylindrical body having the largest diameter at the front end thereof;

the peripheral edge of said front end of said cylindrical body being rounded at a radius of curvature of 5/100 to 10/100 mm in cross section; and the diameter of the rear end of said cylindrical body being smaller than the inner diameter of the hollow barrel so as not to contact with the inner surface of the hollow barrel when the piston is inserted into said hollow barrel.

2. A sliding piston for a syringe according to claim 1, wherein said substantially cylindrical body is provided with a first reduced portion whose diameter is reduced from the front end to an intermediate portion and a second reduced portion whose diameter is reduced from the intermediate portion to the rear end, the degree of reduction in diameter of the second reduced portion being greater than that of the first reduced portion.

3. A sliding piston for a syringe according to claim 2, wherein the contours of said first and second reduced portions in a longitudinal section taken along a plane including the longitudinal axis of the cylindrical body are defined by a straight line and an arc, respectively.

4. A sliding piston for a syringe according to claim 3, wherein said first reduced portion is tapered at an angle in the range of 0.5° to 3.0° with respect to the longitudinal axis of said cylindrical body.

5. A sliding piston for a syringe according to claim 1, wherein said front end of said substantially cylindrical body is provided with a flat conical surface.

6. A sliding piston for a syringe according to claim 1, wherein said front end of said substantially cylindrical body is provided with a surrounding annular flat surface portion substantially perpendicular to the axis of said cylindrical body and a central substantially flattened conical surface portion.

7. A sliding piston for a syringe according to claim 1, wherein said substantially cylindrical body is provided on the rear end thereof with a threaded hole in which a plunger can be screwed, and the minimum thickness defined by the distance of the outer peripheral surface from the peripheral surface of said threaded hole is in the range of 1.0 mm to 4.0 mm.

8. A sliding piston for a syringe according to claim 1, wherein the ratio in the axial length between the first and second reduced portions is in the range of 0.6:1.0–0.9:1, so that said first reduced portion is in contact with said hollow barrel and said second reduced portion is not in contact with said hollow barrel when said piston is inserted in said hollow barrel.

9. A sliding piston for a syringe according to claim 1, wherein said sliding piston comprises an elastic body and a laminated layer thereon, said laminated layer being made of a film selected from a group of tetrafluoroethylene, ethylene-tetrafluoroethylene and supermacromolecular polyethylene resin films.

10. A syringe comprising a hollow barrel, a sliding piston which is inserted in said hollow barrel and a plunger which is screwed in said sliding piston, said piston comprising:

a cylindrical body having the largest diameter at the front end thereof and a threaded hole at the rear end thereof in which said plunger is screwed;

wherein the peripheral edge of the front end of the cylindrical body is rounded at a radius of curvature of 5/100 to 10/100 mm in cross section; and wherein the diameter of the rear end of the cylindrical body is smaller than the inner diameter of said hollow barrel so as not to contact with the inner surface of said hollow barrel when the cylindrical body is inserted therein.

11. A syringe according to claim 10, wherein said cylindrical body is provided with a first reduced portion whose diameter is reduced from the front end to an intermediate portion and a second reduced portion whose diameter is reduced from the intermediate portion to the rear end, so that said first reduced portion is in contact with said hollow barrel and the second reduced portion is not in contact with said hollow barrel when the piston is inserted in said hollow barrel.

12. A syringe according to claim 10, said sliding piston comprising an elastic body and a laminated layer thereon, said laminated layer being made of a film selected from a group of tetrafluoroethylene, ethylene-tetrafluoroethylene and supermacromolecular polyethylene resin films.

* * * * *